(12) United States Patent
Smith

(10) Patent No.: US 6,617,291 B1
(45) Date of Patent: Sep. 9, 2003

(54) OPHTHALMIC AND CONTACT LENS SOLUTIONS

(76) Inventor: Francis X. Smith, 22 Fox Run La., Salem, NH (US) 03079

( * ) Notice: Subject to any disclaimer, the term of this patent is extended or adjusted under 35 U.S.C. 154(b) by 0 days.

(21) Appl. No.: 10/005,659

(22) Filed: Nov. 8, 2001

(51) Int. Cl.[7] .................. A61L 12/10; A61L 12/14; C11D 3/48
(52) U.S. Cl. .............. 510/112; 510/504; 514/839; 514/840; 424/405; 422/28
(58) Field of Search ................ 510/112, 504; 514/839, 840; 424/405; 422/28

(56) References Cited

U.S. PATENT DOCUMENTS

| | | |
|---|---|---|
| 4,136,534 A | 1/1979 | Villa |
| 4,354,952 A | 10/1982 | Riedhammer et al. |
| 4,361,548 A | 11/1982 | Smith et al. |
| 4,525,346 A | 6/1985 | Stark |
| 4,758,595 A | 7/1988 | Ogunbiyi et al. |
| 4,783,488 A | 11/1988 | Ogunbiyi et al. |
| 5,439,572 A * | 8/1995 | Pankow ................ 204/180.1 |
| 5,660,862 A | 8/1997 | Park et al. |
| 5,674,450 A | 10/1997 | Lin et al. |
| 5,719,110 A | 2/1998 | Cook |
| 5,741,817 A | 4/1998 | Chowhan et al. |
| 5,770,582 A | 6/1998 | von Borstel et al. |
| 5,780,450 A | 7/1998 | Shade |
| 5,807,585 A | 9/1998 | Martin et al. |
| 5,854,303 A | 12/1998 | Powell et al. |
| 5,869,468 A | 2/1999 | Freeman |
| 5,925,317 A | 7/1999 | Rogalskyj et al. |
| 6,022,732 A | 2/2000 | Bakhit et al. |
| 6,153,563 A | 11/2000 | Smith et al. |
| 6,162,393 A * | 12/2000 | De Bruiju et al. ............ 422/28 |
| 6,309,596 B1 | 10/2001 | Xia et al. |
| 6,309,658 B1 | 10/2001 | Xia et al. |

FOREIGN PATENT DOCUMENTS

| | | | | |
|---|---|---|---|---|
| EP | WO 00/07634 | * | 2/2000 | ........... A61L/12/14 |

* cited by examiner

*Primary Examiner*—Mark Kopec
*Assistant Examiner*—Brian P. Mruk
(74) *Attorney, Agent, or Firm*—Jaeckle Fleischmann & Mugel, LLP

(57) ABSTRACT

The present invention relates to improved ophthalmic solutions that employ allantoin in order to more effectively preserve solutions and to reduce the degree to which cationic preservatives will deposit on contact lenses. Ophthalmic solutions are here understood to include contact lens treatment solutions, such as cleaners, soaking solutions, conditioning solutions and lens storage solutions, as well as wetting solutions and in-eye solutions for treatment of eye conditions.

8 Claims, No Drawings

OPHTHALMIC AND CONTACT LENS SOLUTIONS

BACKGROUND OF THE INVENTION

The present invention relates to the field of ophthalmic solutions and especially to the aspects of preservative efficacy and comfort after prolonged use. These ophthalmic solutions have been used for some period of time and are available as over the counter products. Solutions that are used in direct contact with corneal tissue such as the delivery of active pharmaceutical agent to the eye, or indirectly, such as the cleaning, conditioning or storage of devices that will come in contact with corneal tissue, such as contact lenses, there is a need to insure that these solutions do not introduce sources of bacterial or other microbial infection. Thus preservatives are included to reduce the viability of microbes in the solution and to lessen the chance of contamination of the solution by the user since many of the solutions are bought, opened, used, sealed and then reused.

State of the art preservative agents include polyhexamethylene biguanide (phmb), polyquad ™, chlorhexidine, and benzalkonium chloride, and the like, all of which at some concentration irritate corneal tissue and lead to user discomfort. Therefore, a solution that employs a given amount of a preservative agent, but which is made more effective by addition of an agent that is not a preservative agent would be desired.

SUMMARY OF THE INVENTION

The present invention relates to improved ophthalmic solutions that employ allantoin in order to more effectively preserve solutions and to reduce the degree to which cationic preservatives will deposit on contact lenses. Ophthalmic solutions are here understood to include contact lens treatment solutions, such as cleaners, soaking solutions, conditioning solutions and lens storage solutions, as well as wetting solutions and in-eye solutions for treatment of eye conditions.

The solutions specifically described herein have 0.001 to about 1 percent of allantoin in combination with other active ingredients useful in ophthalmic solutions such as tonicity agent, buffers, preservatives, surfactants, and antimicrobial agents. The preservatives that are specifically useful are catirnic preservatives such as polyhexamethylene biguanide (phmb), polyquad ™, chlorhexidine, and benzalkonium chloride, as well as other cationic preservatives that may prove useful in the present invention as well. The cationic preservatives are used at effective amounts as preservatives, and in the instance of PHMB from 0.0001 percent by weight to higher levels of about 0.01 weight percent. It was found that an unexpected preservative efficacy was displayed when allantoin was used in conjunction with the cationic preservative. These cationic preservatives can be used in the range of 1 to 100 parts per million, or in amounts of at least one part per million. The other components of the solution are used at levels known to those skilled in the art in order to improve the wearability of lenses and when used directly in the eye, to provide increased resistance to infection. Allantoin used in ophthalmic solution increases preservative efficacy in certain formulations, provides increased resistance to infection in corneal tissue, in certain formulations, and improves the quality of tears in certain formulations.

The formulations may also include buffers such as phosphates, bicarbonate, citrate, borate, ACES, BES, BICINE, BIS-Tris, BIS-Tris Propane, HEPES, HEPPS, irnidazole, MES, MOPS, PIPES, TAPS, TES, and Tricine Surfactants that might be employed include polysorbate surfactants, polyoxyethylene surfactants, phosphonates, saponins and polyethoxylated castor oils, but preferably the polyethoxylated castor oils. These surfactants are commercially available. The polyethoxylated castor oils are sold by BASF under the trademark Cremaphor®.

Specific embodiments might include contact lens solution further comprising a osmotic agent selected from the group consisting of trehalose, mannitol, sorbitol, lactulose, sodium chloride, and propylene glycol. Alternately embodiments might include a solution with between 0.01% and 5.0% glycerin. Still further the invention can include between 0.01% and 2.0% of decanedioic acid and further comprise a sequestering agent selected from the group consisting of ethyltenediaminetetraacetic acid, phosphonates, citrate, gluconate and tartarate.

Allantoin and the other agents used in the present invention are all commercially available, and well enough understood to be formulated into products within the scope of the invention by those skilled in the art.

EXAMPLE 1

Improved Antimicrobical Activity

Formulations containing allantoin were prepared in a 0.1% phosphate buffer. The solutions were made isotonic with sodium chloride and preserved with polyhexamethylene biquanide at 0.0001% and hydrogen peroxide at 0.0060%. Diethylenetriaminepenta(methylenephosphonic acid was added as a stabilizer. The pH was adjusted to 7.0 with either 1 N sodium hydroxide. The in vitro microbicidal activity of the solutions was determined by exposing C. albicans to 10 ml of each solution at room temperature for 4 hours. Subsequently, an aliquot of each solution was serial diluted onto agar plates and incubated for 48 hours at elevated temperatures. At the conclusion of the incubation period the plates are examined for the development of colonies. The log reduction was determined based on a comparison to the inoculum control. The following table provides the results of the in vitro studies.

|  | C albicans log reduction | Improvement |
| --- | --- | --- |
| Allantoin (0.3%) | 1.27, 1.49 | 0.85, 1.08 |
| buffer control | 0.41 |  |

The solution containing allantoin showed an improvement in the activity against C. albicans as compared to the buffer control.

EXAMPLE 2

Acanthamoeba Data

Formulations containing allantoin, bis-tris, carnitine, and 2-amino-2-methyl-1-propanol were prepared in the same buffer matrix as used in Example 1 supra. Polypropylene centrifuge tubes containing 2 mL of test disinfecting solution were inoculated with 0.05 mL of $10^6$ per mL cyst suspension. Two tubes of phosphate buffered saline were inoculated as a positive control. Two tubes of phosphate buffered saline were left uninoculated as negative controls. Appropriate solutions were inoculated as technical controls. All tubes were left at room temperature for two hours. After two hours, 5.0 mL of a neutralizer was added to each tube. One mL was removed from each tube and transferred to a tissue culture flask pre-filled with 9.0 mL peptone-yeast-glucose broth supplemented with antibiotics and heat-killed yeast. This was designated as −1 dilution. The flask was capped and agitated carefully to mix. One mL was removed from the −1 dilution flask and transferred to another tissue culture flask containing 9.0 mL peptone-yeast-glucose broth with antibiotics and heat killed yeast. This was designated as a −2 dilution. Dilutions continued in this manner to a −5 dilution. The tissue culture flasks were incubated on their sides at 35° C. After 14 days, the flasks were examined for the presence of viable trophozoites using an inverted microscope at 200×. The presence of any viable trophozoites in a flask was considered positive growth and was recorded as (+). The absence of viable trophozoites in a flask was considered negative growth and was recorded as (−). Log reduction was estimated based on the difference between the positive control flasks.

When these solutions were tested against *Acanthamoeba castellanii* ATCC 30461 with a two hour exposure the following formulations showed a one log reduction and performed better than the technical commercial control solutions. Formulations using the following components for the respective formulations:

a). allantoin, bis-tris, 2-amino-2-methyl-1-propanol b). carnitine c). allantoin d). allantoin, 2-amino-2-methyl-1-propanol e). allantoin, carnitine, 2-amino-2-methyl-1-propanol The results of this test indicated that allantoin improves the activity of preserved formulations against Acanthamoeba.

EXAMPLE 3

Formulation Preserved Solution for Rinsing, Storage, Reconsitituting Enzyme Tablets A formulation was prepared by dissolving Tricine, Allantoin, Inositol, Disodium edetate, and Polyoxyl 40 Hydrogenated Castor Oil in 80% of the water volume. The pH of the solution was adjusted to 7.3 with 1 N sodium hydroxide. The tonicity of the solution was adjusted with sodium chloride and polyhexamethylene biguanide was added. The solution was diluted to volume with water.

| Constituent | Supplier | % Weight/Volume | Amount |
|---|---|---|---|
| Purified water | | to 80% | 40 mL |
| Tricine | Spectrum | 1.0% | 0.500 g |
| Allantoin | Spectrum | 0.25% | 0.125 g |
| Inositol | Spectrum | 0.1% | 0.50 g |
| Edetate Disodium | Spectrum | 0.055% | 0.0275 g |
| Polyoxyl 40 Hydrogenated Castor Oil | Cremophor RH 40 from BASF Co. | 0.1% | 0.5 mL of 10% |
| Sodium Hydroxide, 1N | | as required for pH adjustment to 7.3 | as required for pH adjustment to 7.3 |
| Purified Water | | to 98% | Dilute to 49 mL |
| Sodium Chloride | Fisher | As required for tonicity adjustment 285 mOsm | As required for tonicity adjustment 285 mOsm |
| Polyhexamethylene-biguanide HCl | 20% w/w solution available under the mark Cosmocil CQ from Avecia | 0.0001% | 50 uL of 0.1% |
| Purified Water | | Balance to 100% | Dilute to 50 mL |

This provides an example of a specific formulation of the present invention but does not fully illustrate the bounds or limits of the invention.

What is claimed is:

1. A contact lens solution comprising 0.001 to 1.0 weight percent allantoin; and at least one part per million of a cationic polymeric preservative chosen from the group consisting of polyhexainethylene biguanide (phmb), chlorhexidne, and benzalkonium chloride.

2. The contact lens solution of claim 1, wherein the concentration of said cationic polymeric preservative is between 1 and 100 parts per million.

3. The contact lens solution of claim 1, further comprising a physiologically compatible buffer selected from the group consisting of phosphate, bicarbonate, citrate, borate, ACES, BES, BICINE, BIS-Tris, BIS-Tris Propane, HEPES, HEPPS, imidazole, MES, MOPS, PIPES, TAPS, TES, and Tricine.

4. The contact lens solution of claim 1, further comprising an osmotic agent selected from the group consisting of trehalose, mannitol, sorbitol, lactulose, sodium chloride, and propylene glycol.

5. The contact lens solution of claim 1, further comprising between 0.01 wt % and 5.0 wt % glycerin.

6. The contact lens solution of claim 1 further comprising between 0.01 wt % and 2.0 wt % of decanedioic acid.

7. The contact lens solution of claim 1 further comprising a wetting agent selected from the group consisting of polysorbate surfactants, polyoxyethylene surfactants, phosphonates, saponins and polyethoxylated castor oils.

8. The contact lens solution of claim 1 further comprising a sequestering agent selected from the group consisting of ethylenediaminetetretic acid, phosphoziates, citrate, gluconate and tartarate.

* * * * *